United States Patent [19]

Heacock et al.

[11] Patent Number: 4,801,198
[45] Date of Patent: Jan. 31, 1989

[54] SLIT LAMP ATTACHMENT

[75] Inventors: Gregory L. Heacock, Bothell; Phillip J. Erickson, Kirkland, both of Wash.

[73] Assignee: Ocular Instruments, Inc., Bellevue, Wash.

[21] Appl. No.: 902,395

[22] Filed: Sep. 5, 1986

Related U.S. Application Data

[63] Continuation-in-part of Ser. No. 773,805, Sep. 9, 1985, abandoned.

[51] Int. Cl.$^4$ ............................................. A61B 3/10
[52] U.S. Cl. ................................... 351/214; 350/255
[58] Field of Search ................. 351/205, 214; 350/255

[56] References Cited

U.S. PATENT DOCUMENTS

| | | | |
|---|---|---|---|
| 1,516,145 | 11/1924 | Bosshardt | 350/255 |
| 1,922,537 | 8/1933 | Fouquet | 350/255 |
| 4,370,033 | 1/1983 | Kani et al. | 351/214 |
| 4,597,649 | 7/1986 | Swaniger et al. | 351/214 |

OTHER PUBLICATIONS

M. W. Gaynon, M.D., "Integrated Projection of Fundus Photographs During Macular Photocoagulation", Arch Ophthalmol, vol. 102, Mar. 1984, pp. 464–465.
B. Jean, M.D. et al., "Simultaneous Fluo-Angioscope for Laser Coagulation in the Macular Area", University Eye Clinic Tubingen, Dept. of Diseases of the Post. Segment, 1 page, with attached photograph.

*Primary Examiner*—John K. Corbin
*Assistant Examiner*—Jay P. Ryan
*Attorney, Agent, or Firm*—Christensen, O'Connor, Johnson & Kindness

[57] ABSTRACT

An attachment for a slit lamp that permits the operator to view the superimposition of an image of a patient's eye and a second image that may comprise a fluorescein angiogram or other photographic image of the patient's eye, or an image formed by a CRT or other display system. The slit lamp includes an objective for forming the first image directed along a first optical path, an eyepiece, being attachable to the objective such that the eyepiece is positioned along the first optical path. The attachment includes a body, a beamsplitter, and an image forming system. The body includes an attachment for attaching the body between the objective and viewing means, and also includes a passage through which the first image can pass along the first optical path to the eyepiece. The beamsplitter is mounted in the body, and positioned in the first optical path. The image forming system projects the second image onto the beamsplitter, such that a portion of the second image is reflected along the first optical path. The image forming system may include a zoom lens system for adjusting the size of the second image. The zoom lens system may comprise a pair of lenses and positioning means including an inner tube having a pair of helical slots and a pair of outer tubes having a pair of longitudinal slots. A beamsplitter positioning device is also provided for permitting the operator to precisely position the first and second images with respect to one another.

11 Claims, 7 Drawing Sheets

SLIT LAMP ATTACHMENT

RELATED APPLICATIONS

This application is a continuation-in-part of application Ser. No. 773,805, filed Sept. 9, 1985 now abandoned.

FIELD OF THE INVENTION

The present invention relates to an attachment for a slit lamp that is particularly useful during laser eye surgery.

BACKGROUND OF THE INVENTION

In recent years, lasers have been increasingly used for surgical operations within the eye. In one type of laser surgery, generally termed photocoagulation, a comparatively lower power laser beam from an argon or other visible spectrum laser is directed into the eye and onto a light absorbing target such as a leaking blood vessel or a retinal detachment. The heating of the target resulting from absorption of the energy of the laser beam results in coagulation of the target with beneficial results to the patient.

To assist a physician in accurately aiming the laser beam, it is common to produce a fluorescein angiogram of the eye prior to treatment. The fluorescein serves to highlight and locate the area surrounding the target. The angiogram is then used during the surgical operation as a guide to correct laser beam aiming. In the past, angiograms have been projected on a wall or otherwise displayed through a slide viewer such that the angiogram can be examined by the surgeon during the laser operation. Such prior techniques, however, require the surgeon to constantly shift his or her viewing between the angiogram and the image formed in the slit lamp. This shifting back and forth of the surgeon's view makes the process more time consuming, and also makes it more difficult to accurately aim the laser.

SUMMARY OF THE INVENTION

The present invention provides a slit lamp attachment that permits the operator of the slit lamp to view the superimposition of an image of a patient's eye and a second image that may comprise a fluorescein angiogram or other photographic image of the patient's eye, or an image formed by a CRT or other display system. An angiogram serves to highlight and locate target areas, and the superimposition of an angiogram image and the image of the patient's eye permits the surgeon to accurately identify and treat the patient's eye during surgery.

In one preferred embodiment, the present invention provides a slit lamp attachment that permits an operator to view the superimposition of a first image of a patient's eye and a second image. The slit lamp includes objective means for forming the first image directed along a first optical path, and viewing means comprising an eyepiece, the viewing means being attachable to the objective means such that the eyepiece is positioned along the first optical path. The first image may therefore be viewed through the eyepiece. The slit lamp attachment comprises a body, a beamsplitter, and an image forming system. The body includes means for attaching the body between the objective means and the viewing means, and also includes a passage through which the first image can pass along the first optical path from the objective means to the viewing means. The beamsplitter is mounted in the body and positioned in the first optical path. The image forming system includes means for forming the second image, and for projecting the second image onto the beamsplitter such that a portion of the second image is reflected by the beamsplitter along the first optical path. The image forming system may include a zoom lens system for adjusting the size of the second image.

DETAILED DESCRIPTION OF THE INVENTION

Figure 1:
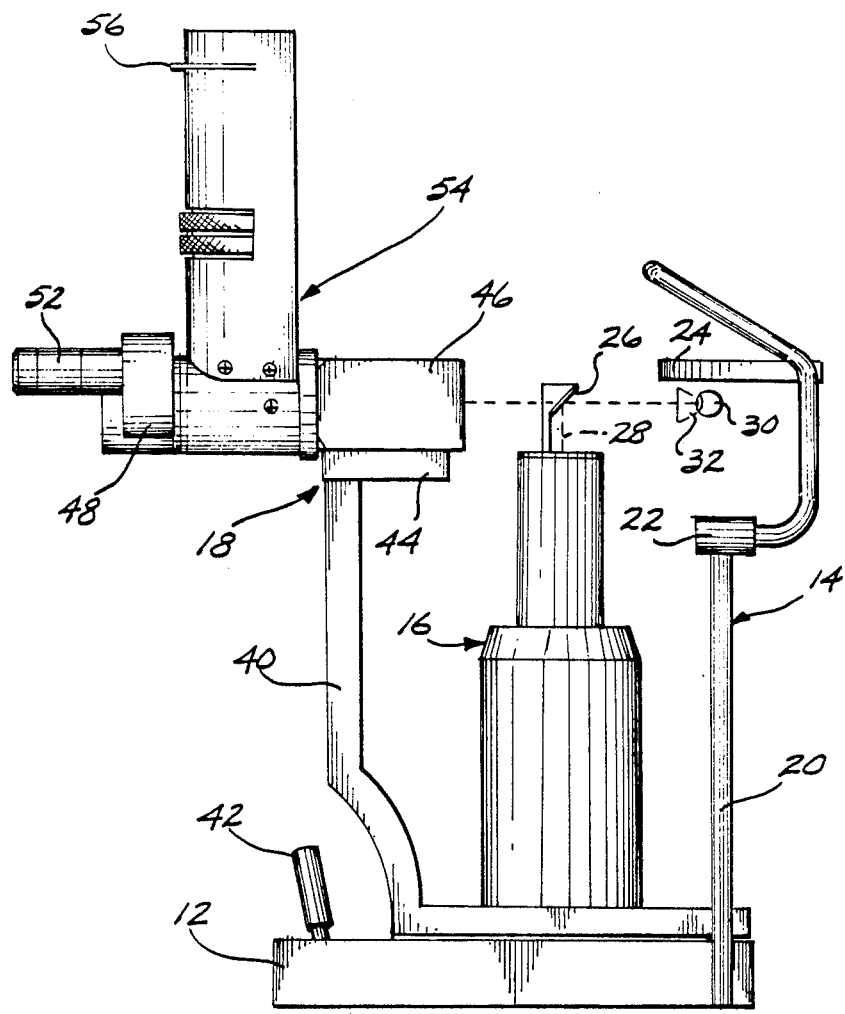
FIG. 1 is a side elevational view of a slit lamp that includes the slit lamp attachment of the present invention.

FIG. 1 presents a schematic view of one embodiment of the slit lamp attachment of the present invention in use in a conventional slit lamp. The slit lamp illustrated in FIG. 1 includes base 12, patient support assembly 14, illumination means 16 and viewing assembly 18. Patient support assembly 14 includes post 20 secured to and upstanding from base 12, chin strap 22 and forehead support 24. Means may be provided for adjusting the positions of the chin strap and forehead support. Illumination means 16 includes mirror 26 and means for directing illumination light and a laser beam along beam path 28, such that the illumination light and laser beam are directed to eye 30 through contact lens 32. The illumination means includes conventional switch means for switching the illumination light on and off. Means may also be provided for adjusting the position and orientation of illumination means 16 with respect to the patient. Other conventional means for introducing illumination light and a laser beam into a patient's eye may also be used.

Figure 3:
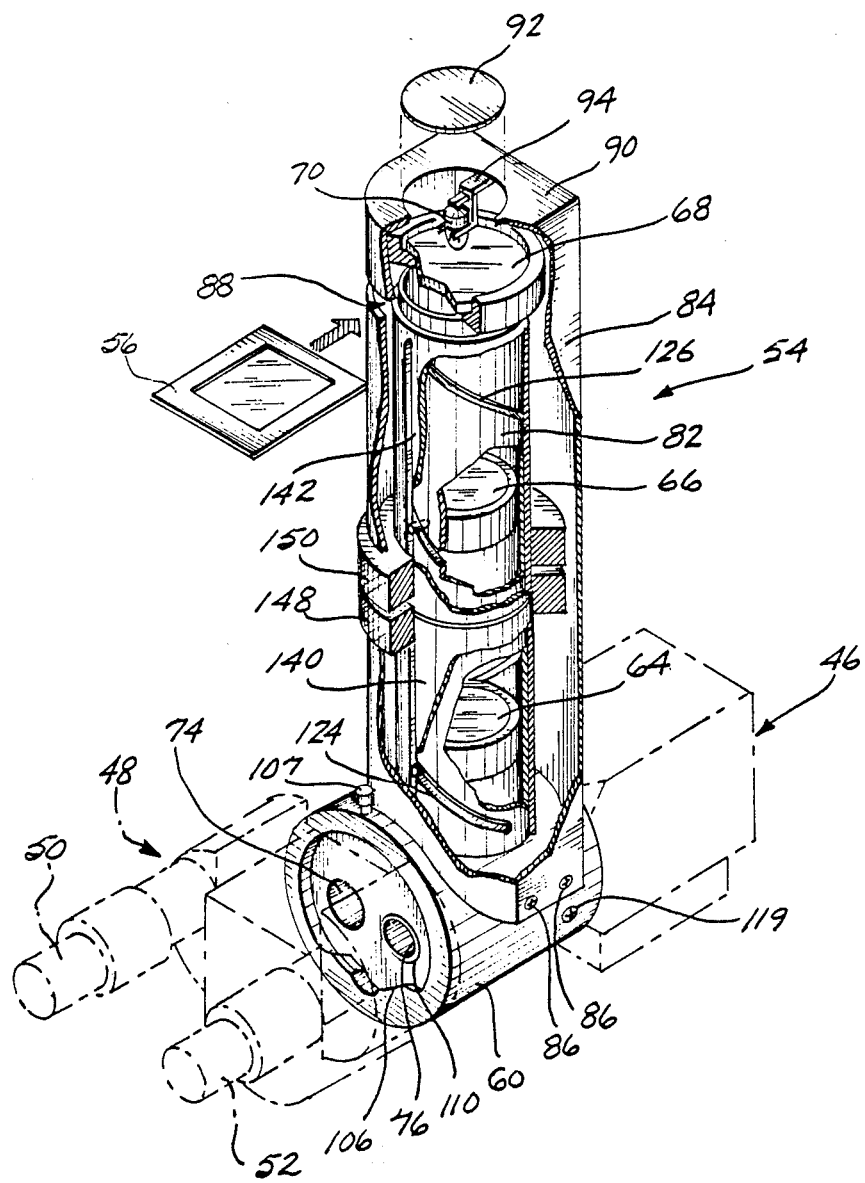
FIG. 3 is a partially cutaway perspective view of the slit lamp attachment; and, FIG. 4 is a combined cross-sectional and side-elevational view of the slit lamp attachment.

Viewing assembly 18 includes arm 40 upstanding from base 12, arm 40 being adjustable by means of control lever 42. Stand 44 is connected to the upper end of arm 40, and objective system 46 is mounted on stand 44. Objective system 46 forms images of a portion of eye 30 for viewing by binocular 48, and typically includes means for varying the magnification of the images. As illustrated in FIG. 3, binocular 48 comprises left and right eyepieces 50 and 52 respectively through which the left and right eyes of an operator can view the patient's eye 30. In the normal use of the slit lamp illustrated in FIG. 1, binocular 48 is mounted directly to objective system 46. However, in accordance with the present invention, attachment 54 is interposed between the objective system and the binocular. Attachment 54 operates to project an image of slide 56 into the optical path of the slit lamp, such that the image of slide 56 is superimposed over the image of the patient's eye. Slide 56, by way of example, may comprise a fluorescein angiogram slide taken of the eye prior to treatment. The fluorescein serves to highlight and locate the target area surrounding the leaking blood vessel, retinal detachment or the like, such that the target area can be more readily identified and accurately treated by the surgeon.

Figure 2:
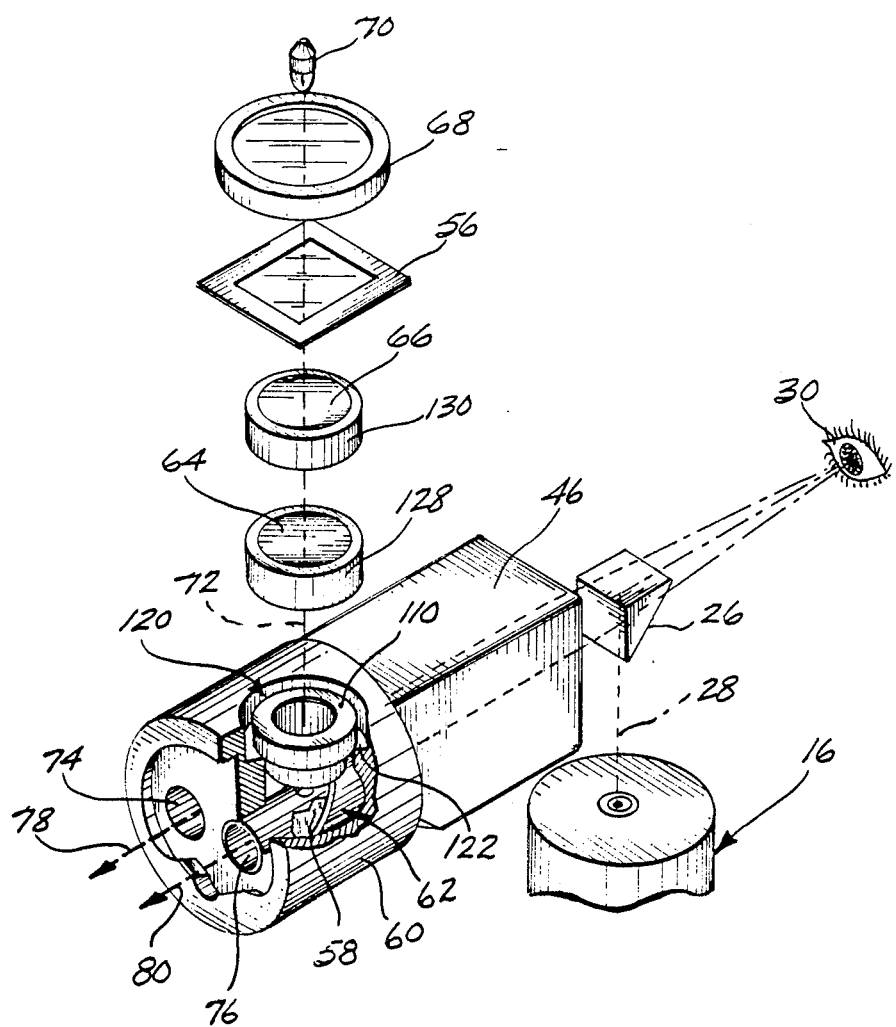
FIG. 2 is a schematic view of the optical elements of the slit lamp attachment.

Referring now principally to FIG. 2, attachment 54 comprises body 60, beamsplitter assembly 62 that includes beamsplitter 58, achromatic lens 64, negative lens 66, diffuser 68 and illumination source 70. Body 60 includes a pair of parallel, axial, cylindrical passages 74 and 76. Objective system 46 is operative to form a pair of images of eye 30, and to direct such images along parallel optical paths 78 and 80 to eyepieces 50 and 52 of binocular 48. Passages 74 and 76 permit such images to pass through body 60 to the binocular. Lenses 64 and 66, diffuser 68 and illumination source 70 comprise a zoom focusing and projection system for slide 56 that projects an image of the slide along optical path 72 onto beamsplitter 58.

The beamsplitter is interposed in optical path 80, and is oriented at an angle of 45° with respect to optical paths 72 and 80. The beamsplitter thereby produces a combined image of eye 30 and slide 56 along optical path 80 that may be viewed through right eyepiece 52. This arrangement wherein the image of slide 56 is introduced into only one of optical paths 78 and 80, and therefore to only one of the eyes of the operator of the slit lamp, is a preferred feature of applicant's invention, inasmuch as it maintains the depth perception of the patient's eye produced by the use of a binocular. In contrast, introduction of the image of slide 56 to both eyepieces of the binocular would result in an identical image of slide 56 presented to both of the operator's eyes, thereby destroying depth perception.

The slit lamp attachment of the present invention includes switch means (not shown) for switching illumination source 70 on and off. The switch means is preferably combined with the means for switching the illumination light provided by an illumination means 16 on and off, such that the operator can conveniently switch between three states: illumination means 16 on and illumination means 70 off, whereby only the patient's eye is visible to the operator; illumination means 70 on and illumination means 16 off, whereby only the image of slide 56 is visible to the operator; and illumination means 16 and illumination means 70 both on, whereby a superimposition of the patient's eye and slide 56 are visible to the operator. The ability to provide all three images to an operator at reasonable brightness levels, and the maintenance of depth perception in the superimposed images, depend upon proper selection of the reflection/transmission values of beamsplitter 58. It has been found that a beamsplitter that is approximately 30% reflective provides the best overall image quality while preserving depth perception. However, beamsplitters up to about 50% reflective have been found to operate in a satisfactory manner.

Figure 4:
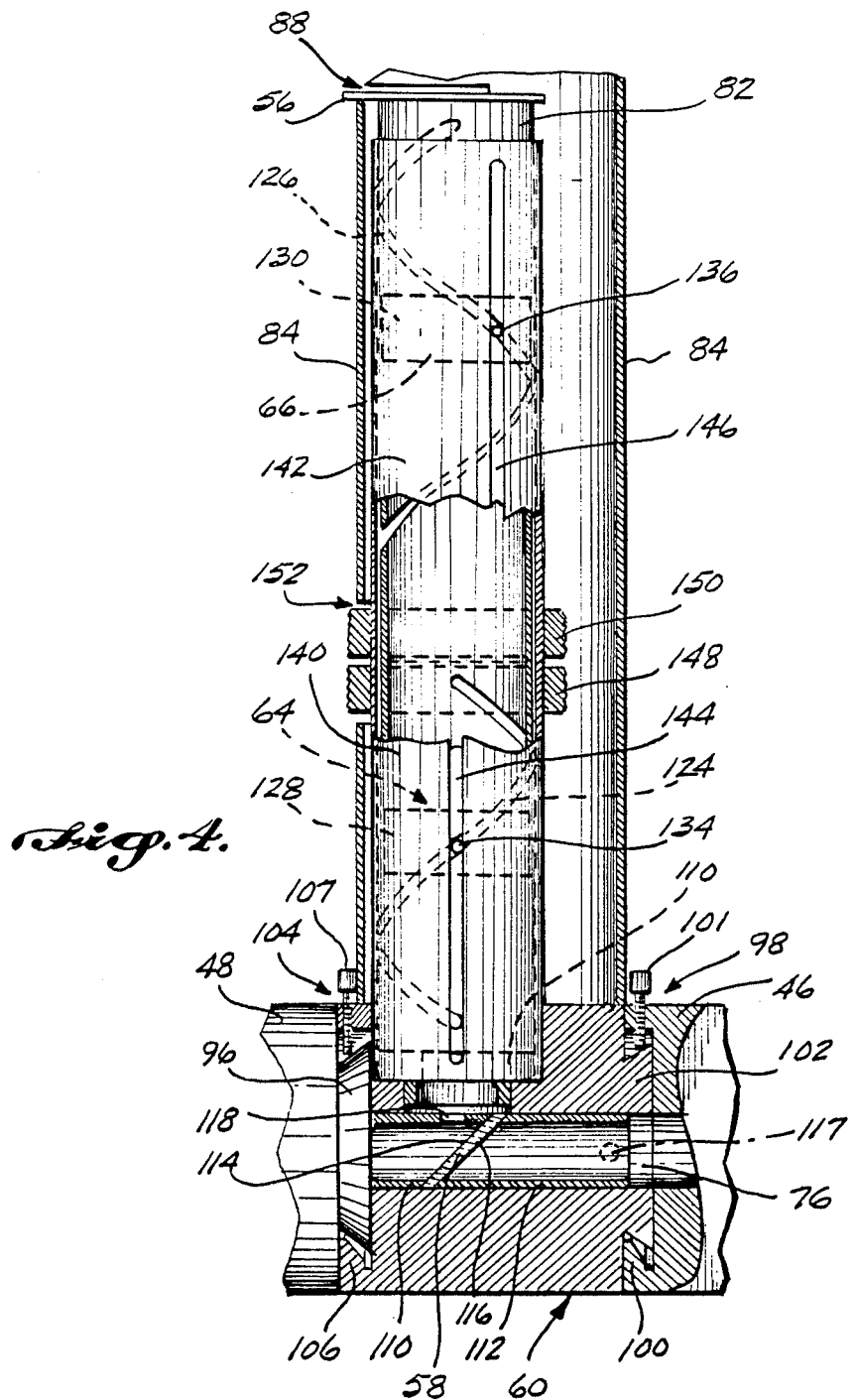

The construction and operation of attachment 54 is illustrated in FIGS. 2-4. Body 60 has a generally cylindrical outer shape, and includes axial passages 74 and 76 described above. In the absence of attachment 54 of the present invention, binocular 48 attaches to objective system 46 by means of a dovetail arrangement (FIG. 4) that includes outwardly flaring projection 96 of binocular 48 and a complementary connector 98 of objective system 46. Connector 98 includes upwardly extending lip 100 and screw 101 for securing projection 96 between lip 100 and screw 101. Body 60 includes flared projection 102 that is essentially identical to projection 96 of binocular 48. Body 60 can thereby be mounted to objective system 46 in a fashion identical to the mounting of binocular 48 to the objective system. Body 60 further includes connector 104 at its opposite end, connector 104 being essentially identical to connector 98 and comprising lip 106 and screw 107. Binocular 48 can therefore be mounted to body 60 in a manner identical to the mounting of binocular 48 to objective system 46. The attachment of the present invention therefore requires no auxiliary means for mounting the attachment to the slit lamp. It is to be understood that the mounting means at either end of body 60 are adapted for the binocular/objective system connection method of a particular slit lamp, and not limited to the specific connection method shown in the illustrated embodiment.

Beamsplitter assembly 62 includes mounting tubes 110 and 112 between which beamsplitter 58 is positioed. Mounting tubes 110 and 112 are preferably fabricated from a single piece of tubing that is cut along a plane oriented at an angle of 45° with respect to the tube axis to produce a pair of complementary 45° mounting surfaces 114 and 116. Beamsplitter 58 is secured to one of the mounting surfaces, preferably to mounting surface 116 of mounting tube 112. Mounting tube 110 includes iris 118 in its upper surface, iris 118 comprising a circular opening positioned above beamsplitter 58, the opening being sized to pass the slide image directed along optical path 72 but to block stray light from striking the beamsplitter. Mounting tube 112 includes lateral openings 117 that may be used by a suitable gripping instrument to rotate the mounting tubes such that iris 118 is centered on optical path 72. The mounting tubes are then locked against rotation by means of screw 119 (FIG. 3), such that the beamsplitter is mounted at a 45° angle with respect to optical paths 72 and 80.

Attachment 54 comprises body 60 and beamsplitter assembly 62, as described above, and further includes mounting tube 82 and case 84 extending upwardly from body 60. Case 84 has a semi-cylindrical cross section, and is fastened directly to body 60 by means of screws 86 (FIG. 3). The upper end of case 84 includes slit 88 into which slide 56 can be inserted. The upper end of case 84 also includes end wall 90 in which cap 92 is formed. Cap 92 provides access to illumination source 70 that is mounted to end wall 90 by tab 94. Diffuser 68 is mounted to case 84 directly beneath illumination source 70, and operates to provide uniform illumination over the area of slide 56.

Mounting tube 82 of attachment 54 comprises a cylindrical tube that is secured at its lower end to mounting ring 108. Mounting ring 108 is mounted within cylindrical opening 120 that is formed in the upper surface of body 60 and that communicates with passage 76. Mounting tube 82 is secured at its upper end to case 84 by any suitable means. Mounting tube 82 includes helical slots 124 and 126, helical slot 124 extending along and around the lower portion of mounting tube 82, and helical slot 126 extending along and around the upper portion of mounting tube 82. Lenses 64 and 66 include respective lens cells 128 and 130 within which the lenses are mounted. Lens cell 128 includes a pair of pins 134 (only one pin shown) extending outwardly in opposite directions from opposite sides of the lens cell. Similarly, lens cell 130 includes a pair of pins 136 (only one pin shown) extending outwardly from lens cell 130. Pins 134 and 136 extend through helical slots 124 and 126, respectively. Lens cells 128 and 130 are dimensioned for a close but sliding fit between the rims and mounting tube 82, such that lenses 64 and 66 remain aligned with optical axis 72 as the lenses move up and down the length of mounting tube 82.

Adjustment tubes 140 and 142 are mounted around and in close sliding contact with mounting tube 82. Adjustment tubes 140 and 142 include longitudinal slots 144 and 146 that extend for nearly the full length of the respective adjustment tubes. Pin 134 extends outward from rim 128, through helical slot 124, as described above, and then into longitudinal slot 144. In a similar manner, pibn 136 extends through helical slot 126 and through longitudinal slot 146. The lower end of adjustment tube 142 abuts directly the upper end of adjustment tube 140. Adjustment tubes 140 and 142 include respective adjustment wheels 148 and 150 respectively. Adjustment wheels 148 and 150 extend through opening 152 of case 184, to provide an operator with access to the adjustment wheels.

The arrangement described above permits simple and convenient adjustment of the positions of the lenses 64 and 66, thereby permitting adjustment of the magnification and focus of the zoom projection system. In particular, rotation of adjustment wheel 148 by an operator causes adjustment tube 140 and helical slot 124 to rotate. Because pin 134 is constrained to move within helical slot 124, the result is that pin 134 and lens 64 move upward or downward within mounting tube 82. In a similar manner, rotation of adjustment wheel 150 results in upward or downward movement of lens 66.

Figure 5:
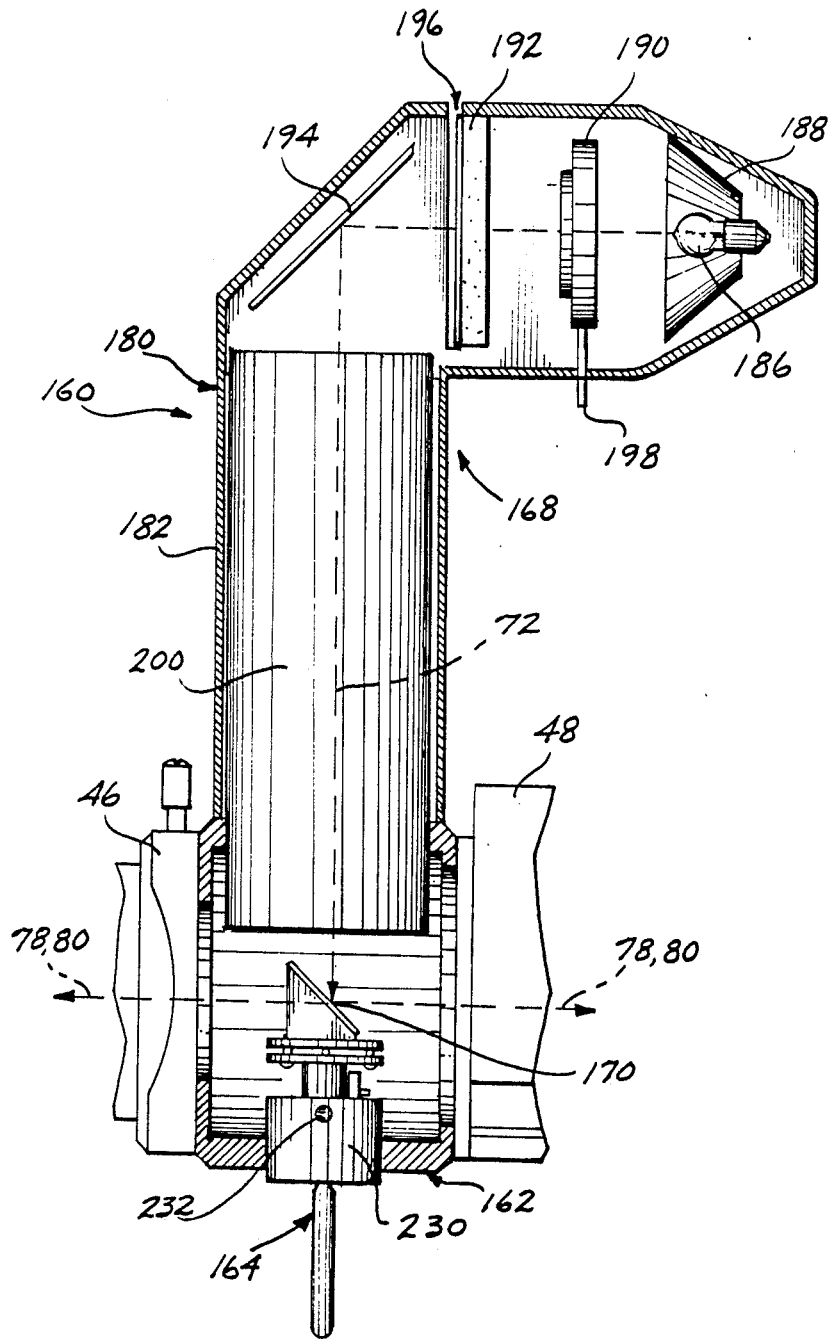
Figure 6:
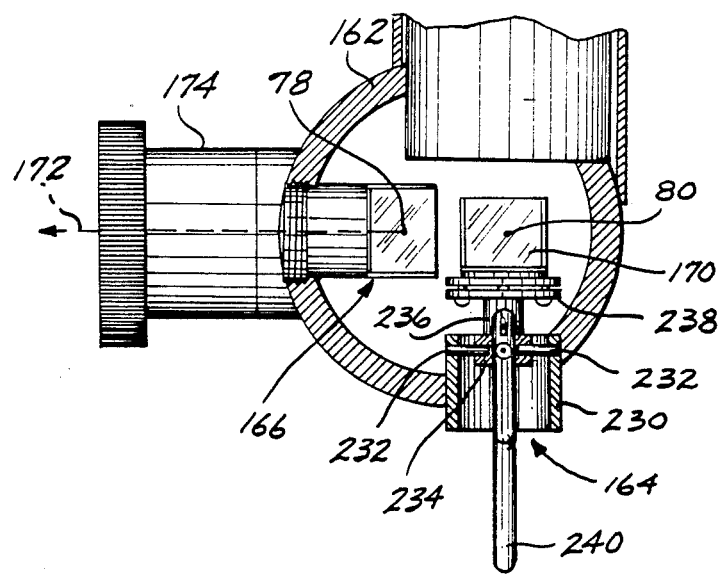

A second preferred embodiment of the slit lamp attachment of the invention is illustrated in FIGS. 5 and 6. In this embodiment, slit lamp attachment 160 comprises body 162, first beamsplitter assembly 164, second beamsplitter assembly 166 and image forming system 168. Body 162 comprises a hollow cylinder, and includes means, such as those shown in FIG. 4, for permitting the body to be secured between objective system 46 and binocular 48. Beamsplitter assembly 164 is mounted within a cylindrical opening in body 162, and includes beamsplitter 170 that is positioned in optical path 80. Beamsplitter 170 therefore combines the eye image projected along optical path 80 by objective means 46 with the image formed by image forming system 168 along optical path 72, and presents the superimposed images to the right eyepiece of binocular 48. First beamsplitter assembly 164 includes positioning means for adjusting the orientation of beamsplitter 170, in order to permit an operator to precisely superimpose the images. Details of the positioning means of the first beamsplitter assembly are described below.

Second beamsplitter assembly 166 is positioned in optical path 78, and operates to reflect a portion of the eye image directed along optical path 78 onto optical path 172. The second beamsplitter assembly is mounted within a lateral, cylindrical opening in body 162. A conventional adapter 164 is secured to the outer surface of body 162, and permits the image on optical path 172 to pass out of the body into an external device, as described in greater detail below.

Image forming system 168 comprises frame 180 that includes column portion 182 extending upward from body 172, and head 184. Mounted within head 184 is a source of illumination 186, reflector 188, mechanical iris 190, diffuser 192 and mirror 194. Head 184 is formed so as to include slot 196 within which a slide may be positioned. Iris 190 includes handle 198 extending through the lower wall of head 184, the handle being provided so as to permit an operator to vary the intensity of the illumination from source 186 reaching diffuser 192. Light passing through the diffuser passes through a slide mounted in slot 196, and the resulting slide image is then reflected by mirror 194 downward along optical path 72. Column 182 preferably comprises a zoom lens system, schematically illustrated by reference numeral 200, that may be similar to the zoom lens system shown in the embodiments of FIGS. 1-4. Thus the intensity or brightness of the image formed by image forming system 168 may be adjusted by means of iris 190, the magnification of such image may be adjusted by means of the zoom lens system, and the positioning of such image with respect to the image on optical path 80 may be adjusted by means of first beamsplitter assembly 164. This arrangement gives the operator of the slit lamp attachment full control over the image formed by image forming system 168.

Figure 7:
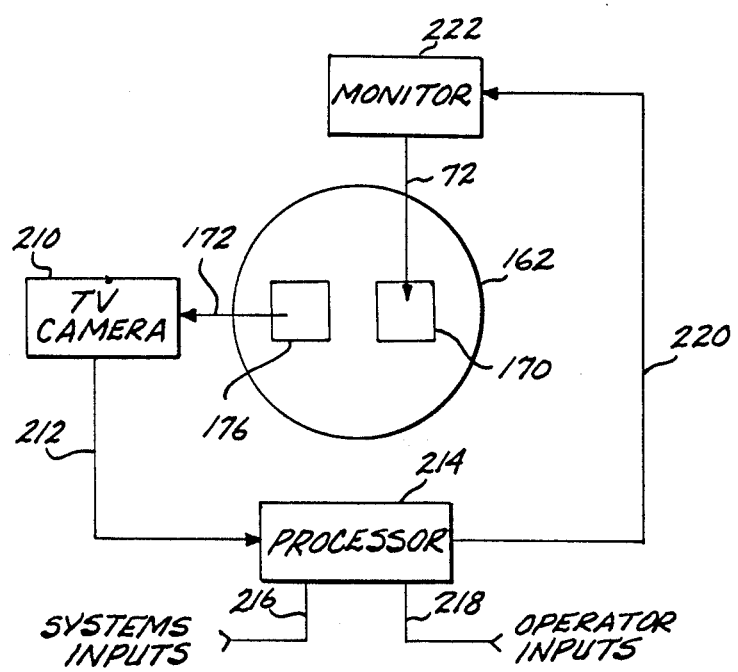

Referring again to FIG. 6, adapter 174 may be used as a conventional monocular observation port, to permit a second opeator to view the image formed by objective system 46. However,the monocular observation port formed by second beamsplitter assembly 166 and adapter 174 can also be used as indicated in FIG. 7 to considerably enhance the versatility of the slit lamp attachment. As illustrated in the embodiment of FIG. 7, the image formed on optical path 172 is input to TV camera 210, and the TV camera converts such image into a video signal on line 212 that is input to processor 214. Processor 214 may combine the video signal with information provided by the slit lamp and/or the operator on lines 216 and 218 respectively, and provide a composite video output signal on line 220 that is input to monitor 222. Monitor 222 may comprise any conventional two-dimensional display system, such as a CRT, liquid crystal display, electroluminescent display, etc. Monitor 222 takes the place of illumination source 186, iris 190, diffuser 192 and slot 196 of the embodiment of FIG. 5, such that the image displayed on monitor 222 is provided along optical path 72, which image is combined by beamsplitter 170 with one of the eye images formed by objective means 46.

Processor 214 may simply annotate the image embodied in the video signal on line 212 with alphanumeric information derived from the system or operator inputs, or may process the video signal, in accordance with such inputs, to produce a modified or enhanced video signal on line 220. System inputs that may be provided on line 216 include, by way of example, information concerning the operationof an associated laser, such as energy level, number of laser actuations, and beam diameter. Annotating the video display with such information permits the operator to work without removing his or her attention from the patient's eye. Operator inputs provided on line 218 may, for example, comprise operator provided specifications relating to the highlighting of specific color, contrasts or shapes. Such highlighting may be beneficial to the operator who wishes to locat or identify specific pathology in a patient's eye. For those situations in which the illumination level in the patient's eye is limited, the brightness level of the video signal can be enhanced in order to produce a clear and easily observed image.

Figure 8:
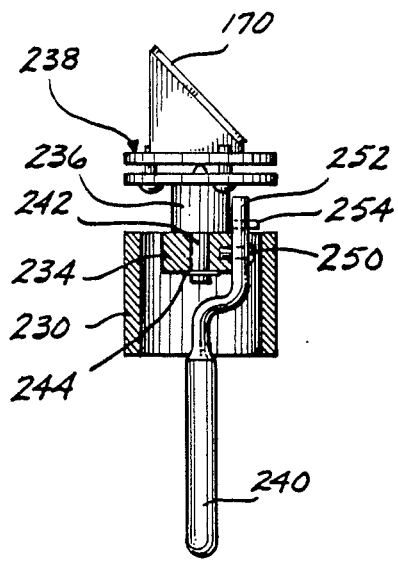

Referring to FIGS. 5, 6 and 8, first beamsplitter assembly 164 comprises cylindrical housing 230 that is secured within the corresponding cylindrical opening in body 162. Pins 232 extend inwardly from opposite sides of housing 230, and mount the remaining components of first beamsplitter assembly 164 for rotation about a first axis defined by pins 232. The components supported by pins 232 include sleeve 234, chord 236, beamsplitter bracket 238 and handle 240. Chord 236 includes stem 242 that extends through a central axial opening in sleeve 234, the stem being secured in the opening by a snap ring 244 such that the chord and the attached bracket and beamsplitter are rotatable about the central axis of stem 242. Arm 240 is pivotally secured to sleeve 234 by pivot pin 250 such that the arm is rotatable about an axis that is offset by 90° with respect to the axis defined by pins 232. The forward end of arm 240 includes a forked portion 252 that engages fixed pin 254 that extends outward from chord 236. Rotation of arm 240 about pivot pin 250 thereby causes rotation of chord 236 and beamsplitter 170 about the central axis of pin 242. First beamsplitter assembly 164 therefore contains two degrees of freedon—rotation about the axis defined by pins 232 and rotation about the central axis of stem 242. Both rotations can be readily controlled by an operator using handle 240, resulting in a simple, convenient and accurate beamsplitter positioning mechanism for permitting the operator of the slit lamp attachment to precisely position the two images with respect to one another.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims The embodiments of the invention in which an exclusive property or privilege is claimed are defined as follows:

1. A slit lamp attachment that permits an operator to view the superimposition of a first image of a patient's eye and a second image, the slit lamp comprising objective means for forming the first image directed along a first optical path, and viewing means comprising an eyepiece, the objective means and the viewing means including an objective connector and a viewing connector respectively, the objective connector and the viewing connector being adapted to connect the viewing means directly to the objective means, the viewing means being attachable to the objective means such that the eyepiece is positioned along the first optical path to permit viewing of the first image through the eyepiece, the slit lamp attachment comprising:
 (a) a body including a first connector adapted to cooperate with the objective connector to attach the body to the objective means and a second connector adapted to cooperate with the viewing connector for attaching the viewing means to the body, the first connector being substantially similar to the viewing connector and the second connector being substantially similar to the objective connector, the body further comprising a passage through which the first image can pass along the first optical path from the objective means to the viewing means;
 (b) a beamsplitter mounted in the body and positioned in the first optical path; and
 (c) an image forming system comprising means for forming the second image and for projecting the second image onto the beamsplitter such that a portion of the second image is reflected by the beamsplitter along the first optical path.

2. The slit lamp attachment of claim 1, wherein the image forming system comprises a zoom lens system including means for adjusting the size of the second image in relation to the size of the first image.

3. The slit lamp attachment of claim 1, further comprising means for switching the image forming system between on and off states, and wherein the reflection/transmission characteristics of the beamsplitter are selected such that the first image may be viewed through the viewing means when the image forming system is in its off state, and the superimposition of the first and second images may be viewed through the viewing means when the image forming system is in its on state.

4. The slit lamp attachment of claim 3, wherein the beamsplitter is approximately thirty percent reflective.

5. The slit lamp attachment of claim 1, wherein the objective means forms a pair of first images directed respectively along a pair of first optical paths, wherein the viewing means comprises a binocular comprising two eyepieces, the binocular being attachable to the objective means such that the two eyepieces are positioned along the respective first optical paths to permit viewing of the pair of first images through the respective eyepieces, wherein the body includes passage means through which the first images can pass along the respective first optical paths from the objective means to the binocular, and wherein the beamsplitter is positioned in only one of the first optical paths.

6. The slit lamp attachment of claim 5, wherein the image forming system comprises a zoom lens system including means for adjusting the size of the second image in relation to the size of the first image.

7. The slit lamp attachment of claim 5, further comprising means for switching the image forming system between on and off states, and wherein the reflection/transmission characteristics of the beamsplitter are selected such that the first images may be viewed through the binocular when the image forming system is in its off state, and the superimposition of the first and second images may be viewed through the binocular when the image forming system is in its on state.

8. The slit lamp attachment of claim 7, wherein the beamsplitter is approximately 30% reflective.

9. A slit lamp attachment that permits an operator to view the superimposition of a first image of a patient;s eye and a second image, the slit lamp comprising objective means for forming the first image directed along a first optical path, and viewing means comprising an eyepiece, the viewing means being attachable to the objective means such that the eyepiece is positioned along the first optical path to permit viewing of the first image through the eyepiece, the slit lamp attachment comprising:
 (a) a body including means for attaching the body between the objective means and the viewing means and a passage through which the first image can pass along the first optical path from the objective means to the viewing means;
 (b) a beamsplitter mounted in the body and positioned in the first optical path; and,
 (c) an image forming system comprising means for forming the second image and for projecting the second image onto the beamsplitter such that a portion of the second image is reflected by the beamsplitter along the first optical path, the image forming system including means for mounting a transparency that may comprise a photographic image of the patient's eye, illumination means for illuminating the transparency, and means for receiving light from the illuminated transparency and for forming said light into the second image.

10. The slit lamp attachment of claim 9, further comprising means for switching the illumination means between on and off states, and wherein the reflection/transmission characteristics of the beamsplitter are selected such that the first image may be viewed through the viewing means when the illumination means is in its off state, and the superimposition of the first and second images may be viewed through the viewing means when the illumination means is in its on state.

11. The slit lamp attachment of claim 10, wherein the beamsplitter is approximately 30% reflective.

* * * * *